United States Patent
Sadek et al.

(10) Patent No.: US 8,350,578 B2
(45) Date of Patent: Jan. 8, 2013

(54) WIRING NANOSCALE SENSORS WITH NANOMECHANICAL RESONATORS

(75) Inventors: Akram Sarwat Sadek, Somerset (GB); Rassul Bulatovich Karabalin, North Hills, CA (US); Michael L. Roukes, Pasadena, CA (US); Sotirios K. Masmanidis, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 505 days.

(21) Appl. No.: 12/708,360

(22) Filed: Feb. 18, 2010

(65) Prior Publication Data

US 2010/0219914 A1 Sep. 2, 2010

Related U.S. Application Data

(60) Provisional application No. 61/208,805, filed on Feb. 27, 2009.

(51) Int. Cl.
G01R 29/22 (2006.01)
G01R 23/00 (2006.01)
H01L 41/00 (2006.01)

(52) U.S. Cl. ............ 324/633; 324/76.49; 324/109; 310/311

(58) Field of Classification Search .......... 324/663, 324/76.49, 109; 310/311
See application file for complete search history.

(56) References Cited

U.S. PATENT DOCUMENTS

| | | | | |
|---|---|---|---|---|
| 6,803,840 B2* | 10/2004 | Hunt et al. | ............ | 333/186 |
| 7,349,590 B2* | 3/2008 | Mozdy | ............ | 385/12 |
| 7,434,476 B2* | 10/2008 | Tang et al. | ............ | 73/777 |
| 7,552,645 B2* | 6/2009 | Bargatin et al. | ............ | 73/777 |
| 7,555,938 B2* | 7/2009 | Bargatin et al. | ............ | 324/76.11 |
| 7,617,736 B2* | 11/2009 | Tang et al. | ............ | 73/777 |
| 7,918,935 B2* | 4/2011 | Park et al. | ............ | 117/68 |
| 8,174,352 B2* | 5/2012 | Parpia et al. | ............ | 73/204.26 |
| 2008/0314149 A1* | 12/2008 | Rueger | ............ | 324/649 |
| 2009/0087663 A1* | 4/2009 | Park | ............ | 428/408 |
| 2009/0206987 A1* | 8/2009 | Aubin et al. | ............ | 340/5.8 |
| 2010/0056851 A1* | 3/2010 | Wang et al. | ............ | 600/25 |
| 2011/0001392 A1* | 1/2011 | Masmanidis et al. | ............ | 310/316.03 |

OTHER PUBLICATIONS

Bargatin, I. et al., Efficient electrothermal actuation of multiple modes of high-frequency nanoelectromechanical resonators, Applied Physics Letters, (2007), 093116-1-093116-3, vol. 90.

Beck, R. et al., Strain-sensing cryogenic field-effect transistor for integrated strain detection in GaAs/AlGaAs microelectromechanical systems, Appl. Phys. Lett., Jun. 24, 1996, pp. 3763-3765, vol. 68, Issue No. (26).

(Continued)

Primary Examiner — Timothy J Dole
(74) Attorney, Agent, or Firm — Gates & Cooper LLP

(57) ABSTRACT

A system, device, method, and apparatus provide the ability to wire a voltage sensitive device to a nanoelectromechanical system (NEMS) resonator. A voltage sensitive device is configured to detect one or more voltage signals and output one or more electrical potentials in real-time. An array of piezoelectric NEMS resonators (with each resonator tuned to a unique frequency) is used to receive the output electrical potentials and convert each output electrical potential to a corresponding resonance frequency varying signal. The output signal from each resonator varies in linear proportion to the resonator's corresponding frequency variation arising from the applied electrical potential. The frequency varying signals are multiplexed together into a single readout signal path that is monitored to determine variations in vibrational amplitude. A demodulation device deconvolves the multiplexed frequency varying signals to recover and uniquely identify the output electrical signal.

14 Claims, 12 Drawing Sheets

OTHER PUBLICATIONS

Carr, D. et al., Fabrication of nanoelectromechanical systems in single crystal silicon using silicon on insultor substrates and electron beam lithography, J. Vac. Sci. Technol. B, Nov./Dec. 1997, pp. 2760-2763, vol. 15, Issue No. (6).

Cleland, A. et al., Noise processes in nanomechanical resonators, Journal of Applied Physics, Sep. 1, 2002, pp. 2758-2769, vol. 92, Issue No. 5.

Cleland, A. et al., A nanometre-scale mechanical electrometer, Nature, Mar. 12, 1998, pp. 160-162, vol. 392, Nature Macmillan Publishers Ltd.

Craighead, H., Nanoelectromechanical Systems, Science, Nov. 24, 2000, pp. 1532-1535, vol. 290.

Curie, M., Developpement par compression de l'electricite polaire dans les cristaux hemiedres a faces inclinees, Bulletin de la Societe mineralogique de France, (1880), pp. 90-93.

Devoe, D., Piezoelectric thin film micromechanical beam resonators, Sensors and Actuators A, (2001), pp. 263-272, vol. 88.

Ekinci, K. et al., Electromechanical Transducers at the Nanoscale: Actuation and Sensing of Motion in Nanoelectromechanical Systems (NEMS), Small, (2005), pp. 786-797, vol. 1, Issue No. 8-9.

Fon, W. et al., Nanoscale, Phonon-Coupled Calorimetry with Sub-Attojoule/Kelvin Resolution, Nano Letters, (2005), pp. 1968-1971, vol. 5, Issue No. 10.

Fricke, K., Piezoelectric properties of GaAs for application in stress transducers, J. Appl. Phys., Jul. 15, 1991, pp. 914-918, vol. 70, Issue No. (2).

Fritz, J. et al., Translating Biomolecular Recognition into Nanomechanics, Science, Apr. 14, 2000, pp. 316-318, vol. 288.

Husain, A. et al., Nanowire-based very-high-frequency electromechanical resonator, Applied Physics Letters, Aug. 11, 2003, pp. 1240-1242, vol. 83, Issue No. 6.

Jun, S. et al., Electrothermal tuning of Al-SiC nanomechanical resonators, Nanotechnology, (2006), pp. 1506-1511, vol. 17, Institute of Physics Publishing.

Knobel, R. et al., Piezoelectric displacement sensing with a single-electron transistor, Applied Physics Letters, Sep. 16, 2002, pp. 2258-2260, vol. 81, Issue No. 12.

Lahaye, M. et al., Approaching the Quantum Limit of a Nanomechanical Resonator, Science, Apr. 2, 2004, pp. 74-77, vol. 304.

Lonergan, M. et al., Array-Based Vapor Sensing using Chemically Sensitive, Carbon Black-Polymer Resistors, Chem. Mater, 1996, pp. 2298-2312, vol. 8.

Metzger, C. et al., Cavity cooling of a microlever, Nature, Dec. 23/30, 2004, pp. 1002-1005, vol. 432, Nature Publishing Group.

Piekarski, B. et al., Surface micromachined piezoelectric resonant beam filters, Sensors and Actuators A, (2001), pp. 313-320, vol. 91.

Roukes, M. et al., Mechanical Computation, Redux?, Electron Devices Meeting, Dec. 13-15, 2004, pp. 539-542, IEDM Technical Digest, IEEE International.

Rueckes, T. et al., Carbon Nanotube-Based Nonvolatile Random Access Memory for Molecular Computing, Science, Jul. 7, 2000, pp. 94-97, vol. 289.

Rugar, D. et al., Mechanical Parametric Amplification and Termomechanical Noise Squeezing, Physical Review Letters, Aug. 5, 1991, pp. 699-702, vol. 67, Issue No. 6.

Soderkvist, J., Similarities between piezoelectric, thermal and other internal means of exciting vibrations, J. Micromech. Microeng., (1993), pp. 24-31, vol. 3.

Yang, Y. et al., Zeptogram-Scale Nanomechanical Mass Sensing, Nano Letters 6, 583, Mar. 15, 2006, pp. A-D.

Zhang, Y., Sensitivity of a piezoelectric micromechanical displacement detector based on the radio-frequency single-electron transistor, Journal of Applied Physics, Dec. 15, 2002, pp. 7550-7555, vol. 92, Issue No. 12.

* cited by examiner

WIRING NANOSCALE SENSORS WITH NANOMECHANICAL RESONATORS

CROSS-REFERENCE TO RELATED APPLICATIONS

This application claims the benefit under 35 U.S.C. Section 119(e) of the following commonly-assigned U.S. provisional patent application(s), which is/are incorporated by reference herein:

Provisional Application Ser. No. 61/208,805, filed on Feb. 27, 2009, by Akram S. Sadek, Rassul Karabalin, Michael L. Roukes, and Sotirios K. Masmanidis, entitled "Piezoelectric, Voltage-Sensitive Nanomechanical Systems for Frequency-Modulated, Multiplexed Electrical Signal Transmission in Extracellular Electrode Arrays for Neural Recording Applications".

This application is related to the following commonly-assigned patent applications, which applications are incorporated by reference herein:

U.S. patent application Ser. No. 11/830,653, entitled "HIGHLY EFFICIENT, CHARGE DEPLETION-MEDIATED, VOLTAGE-TUNABLE ACTUATION EFFICIENCY AND RESONANCE FREQUENCY OF PIEZOELECTRIC SEMICONDUCTOR NANOELECTROMECHANICAL SYSTEMS RESONATORS", by Sotirios K. Masmanidis, Rassul Karabalin, and Michael L. Roukes, filed on Jan. 10, 2008, which application claims priority to the following provisional application which is incorporated by reference herein: Provisional Application Ser. No. 60/834,054, filed on Jul. 28, 2006, by Sotirios K. Masmanidis, Rassul Karabalin, and Michael L. Roukes, entitled "D-NEMS: Highly efficient, charge depletion-mediated, voltage-tunable actuation efficiency and resonance frequency of piezoelectric semiconductor nanoelectromechanical systems resonators"; and U.S. patent application Ser. No. 12/335,847, entitled "MICROMACHINED NEURAL PROBES", by Sotirios K. Masmanidis, Jiangang Du, Michael L. Roukes, and Gilles J. Laurent, filed on Dec. 16, 2008, which application claims priority to the following provisional application which is incorporated by reference herein: Provisional Application Ser. No. 61/007,990, filed on Dec. 17, 2007, by Sotirios K. Masmanidis, Jiangang Du, Michael L. Roukes, and Gilles J. Laurent, entitled "Micromachined, double-sided, three-dimensional electrode arrays, fabricated from very thin silicon wafers, for electrophysiological recording and stimulation".

BACKGROUND OF THE INVENTION

1. Field of the Invention

The present invention relates generally to semiconductors, and in particular, to a method, apparatus, and device for wiring nanomechanical resonators to nanoscale sensors.

2. Description of the Related Art (Note: This application references a number of different publications as indicated throughout the specification by reference numbers enclosed in brackets or, e.g., [x] or superscript. A list of these different publications ordered according to these reference numbers can be found below in the section entitled "References."Each of these publications is incorporated by reference herein.)

A multitude of promising nanoscale electronic devices have been developed for the implementation of gain[1], digital logic[2] and analog sensing.[3-5] Yet far less attention has been directed on how to interface systems built from these components with the macroscopic world.[6-9] The top-down wiring problem raises several challenges related to the integration of very large systems with a miniscule footprint. This is especially apparent for sensors based on carbon nanotubes[3], semiconductor nanowires[4], nanoelectromechanical systems[5] and other devices, where the number of readout channels scales in direct proportion to the number of components. Sensor arrays based on these devices have the ability to allow real-time, parallel detection of electrical potentials at thousands of different sites in vivo.[4,10,11]

In his lectures on computation, Richard Feynman speculated that the wiring problem might be tackled by an optical interconnection system through free space, acted on by frequency-sensitive components within the device architecture.[12]

In view of the above, what is needed is the capability for wiring nanoscale sensors arrays to the macroscopic world.

SUMMARY OF THE INVENTION

Nanoscale integrated circuits and sensors require methods for unobtrusive interconnection with the macroscopic world to fully realize their potential. One or more embodiments of the invention provide a nanoelectromechanical system that has the potential to solve the wiring problem by enabling information from multisite sensors to be multiplexed onto a single output line. The basis for this method is a mechanical Fourier transform mediated by piezoelectrically coupled nanoscale resonators. Embodiments allow sensitive, linear, and real-time measurement of electrical potentials from conceivably any voltage-sensitive device. This novel method for wiring nanoscale devices enables minimally invasive implantable sensors with thousands of channels for in vivo medical diagnostics, neuronal recording and electrochemical sensing.

BRIEF DESCRIPTION OF THE DRAWINGS

Referring now to the drawings in which like reference numbers represent corresponding parts throughout:

FIG. 7a illustrates a neural probe that can be used in accordance with one or more embodiments of the invention;

FIG. 7b illustrates the detection of extracellular neuronal action potentials in a locust ganglion preparation using the setup in FIG. 7a;

FIG. 7c illustrates a measurement/detection of an artificially generated signal in saline solution using the neural probe coupled to the NEMS device of FIG. 7a;

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview

Embodiments of the present invention provide a new paradigm for wiring nanoscale sensor arrays to the macroscopic world, employing frequency-sensitive nanoelectromechanical systems (NEMS) coupled to a single output line (output line is also known as an output path or signal transmission line). Potentially, thousands of sensor channels could be multiplexed in parallel, thereby greatly alleviating the wiring constraints that arise with scaling up device complexity.

Detailed Description

One or more embodiments of the invention may be viewed as conceptually similar to the mechanism of action of the cochlea in the inner ear. In the human cochlea the basilar and tectorial membranes couple to the three rows of piezoelectric outer hair cells to form a bank of resonant elements that range from 20 to 20,000 Hz in frequency.[13] The inner hair cells form the electromechanical sensing elements, and can detect deflections as small as a few Angstroms.[14] Incoming sound is decomposed in the cochlea by the resonant elements, and variations in the power of the signal at different frequencies are transmitted through individual nerve channels via the respectively coupled inner hair cells.[15]

Embodiments of the invention rely on the inverse case, coupling electrical signals from individual sensor devices to a bank of piezoelectric nanomechanical resonators, each resonating at a unique frequency. The analog signals vary the amplitude of the mechanical resonance in a linear fashion, and optical interferometry is used to detect the mechanical motion from all the resonators concurrently. External demodulation of the optical signal can reveal the variations in power at each frequency, and hence can recover the original multiplexed signals in real-time and in an addressable manner.

Figure 1:
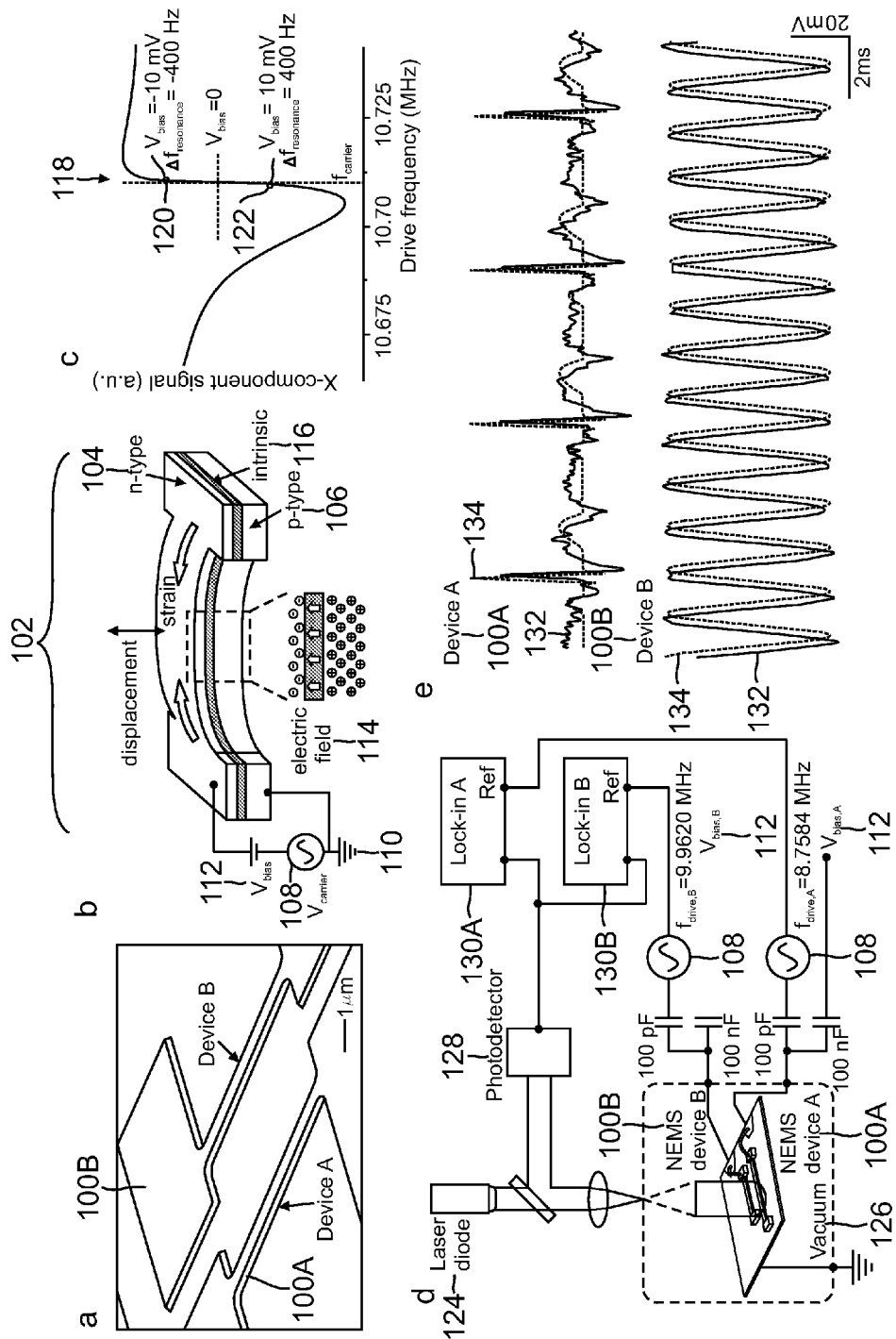
FIG. 1a illustrates two devices that provide a nanoscale piezoelectric beam in accordance with one or more embodiments of the invention.
FIG. 1b illustrates a cross section of the devices of FIG. 1a in accordance with one or more embodiments of the invention.
FIG. 1c illustrates an X-component of the resonance plot of a NEMS resonator device when driven nonlinearly in accordance with one or more embodiments of the invention.
FIG. 1d illustrates a schematic of an experimental setup to demonstrate multiplexing through a nanomechanical transducer in accordance with one or more embodiments of the invention.
FIG. 1e shows demodulated signals transduced from the devices of FIG. 1a in accordance with one or more embodiments of the invention.

FIGS. 1a-1d illustrate a piezoelectric NEMS and nanomechanical Fourier transform in accordance with one or more embodiments of the invention. The structural element 100A and 100B provides a nanoscale piezoelectric beam,[16] as shown in FIG. 1a. The devices 100A and 100B are fabricated from epitaxially grown GaAs, and can be created in a variety of forms. The different types of NEMS devices that can be created are described in detail in U.S. patent application Ser. No. 11/830,653 which is incorporated by reference herein.

For example, the NEMS device may consist of/comprise a movable/resonant member that includes a region of low conductivity over which an electric field is developed. The width of the region (referred to as region width) is within a factor of ten (10) of a thickness of the NEMS device. Such a region of low conductivity may be a depletion layer. In addition, the region may be formed between a junction that incorporates piezoelectric material. In one or more embodiments, such a junction may be formed by differently doped semiconductors. For example, the junction may be a PIN diode, a p-type/ n-type junction, a p-n-p type junction, or a n-p-n type junction.

FIG. 1b illustrates a cross section of an example of a PIN diode type of NEMS resonator in accordance with embodiments of the invention. As depicted in the cross section in FIG. 1b, the NEMS resonator can be a 200 nm thick pin diode 102, with the n-104 and p-106 doped layers connected to the voltage source 108 and ground 110, respectively. Biasing (i.e., via $V_{bias}$ 112) the pin junction 102 results in an electric field 114 that is concentrated across the ~50 nm thick charge intrinsic depletion region 116. The transverse electric field 114 induces a longitudinal piezoelectric strain within the depletion layer 116, which can be used to resonantly excite the flexural mode of the beam 100 through application of a radio frequency (rf) drive. Accordingly, the electric field 114 across the pin junction 102 generates longitudinal piezoelectric strain. An actuating radiofrequency potential, $V_{carrier}$ 108, drives the beam to resonance. A slowly varying potential, $V_{bias}$ 112 modulates the baseline stress in the beam and tunes the resonance frequency.

Figure 2:
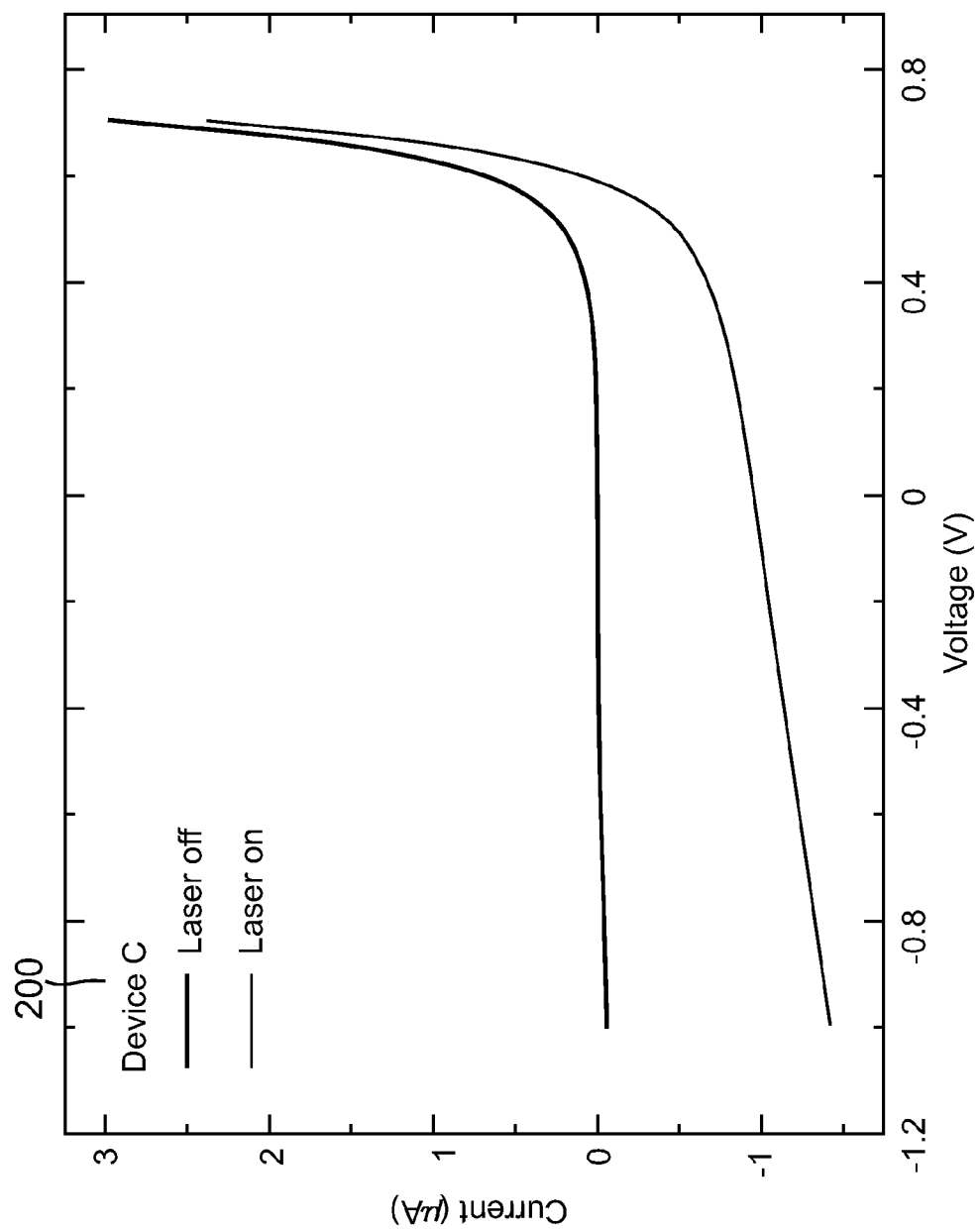
FIG. 2 illustrates the current-voltage characteristics of devices under laser illumination in accordance with one or more embodiments of the invention.

The high resistance of the depletion layer 116 means these devices exhibit very low power dissipation during actuation, on the order of 1 nW or less (as illustrated in FIG. 2 which shows the current-voltage characteristics of devices under laser illumination in accordance with one or more embodiments of the invention). Thus, in FIG. 2, the NEMS devices 100 are constructed as pin diodes 102, and thus share their I-V characteristics and high resistance properties. Although the energy of the diode laser used in the interferometric readout (904 nm) is less than the band gap of GaAs, there may still be a small amount of current generated when the devices are irradiated. Thus, under operating conditions, the impedence of the devices can be reduced, albeit still high. As shown for device C 200, the resistance dropped from 16 MΩ to 2.1 MΩ under illumination. This translates into a power dissipation of ~1 nW when driven in the regime of nonlinear resonance.

Figure 3:
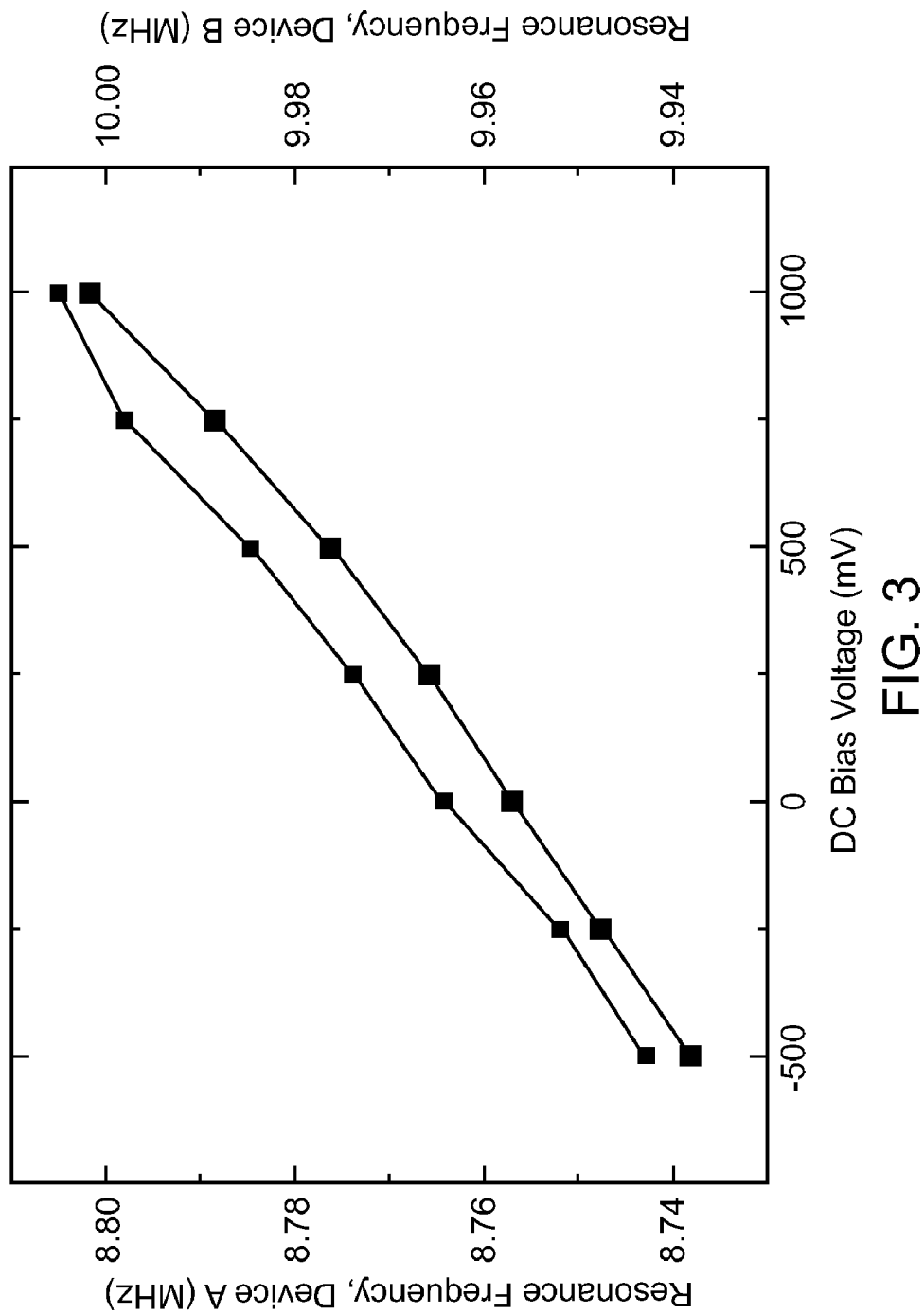
FIG. 3 illustrates the resonance frequency versus the bias voltage for the devices of FIG. 1a in accordance with one or more embodiments of the invention.

As described in copending application Ser. No. 11/830,653 which is incorporated by reference above, the resonance frequency of piezoelectrically coupled NEMS resonators are sensitive to an applied electrical potential.[16] This phenomenon arises from the clamped-clamped boundary conditions of the suspended beam structure, which lead to the conversion of piezoelectric strain into compressive or tensile stress, and modulation of the natural vibrational frequency of the structure. Importantly, this shift is linearly proportional to applied voltage 108, with a slope of approximately 40 kHz per volt for these fabricated devices. FIG. 3 demonstrates such a linear proportion with resonanace frequency tuning in NEMS via a piezoelectric effect. In this regard, FIG. 3 illustrates the resonance frequency versus the bias voltage for devices A 100A (left plot) and B 100B (right plot). Resonance frequency corresponds to the peak amplitude in a frequency-swept measurement carried out with a network analyzer. All potentials are measured with respect to the negative 104 (i.e., top) terminal of the pin junction 102 comprising the nanomechanical structures. The frequency-voltage curve is linear with a slope of approximately 40 kHz/volt for both devices 100A and 100B, signifying the tuning effect is independent of device length.

One or more embodiments of the present invention use this frequency tuning effect to transduce time-varying electrical potentials that might originate from nanoscale sensors of electrophysiological activity. Embodiments indirectly track frequency by operating the resonator at a fixed rf driving frequency and monitoring variations in oscillation amplitude that are manifested as the bias signal shifts the position of the resonance peak. In the small bias regime the demodulated signal amplitude can be expressed as:

$$A(t) = -[d_{31}\eta(Q, V_{drive})/2\pi h^2]\sqrt{3E/\rho} \cdot V_{bias}(t) \quad (1)$$

where $\eta(Q, V_{drive})$ is the slope of the resonance curve represented in FIG. 1c, which is dependent on the quality factor and drive amplitude; E, ρ and $d_{31}$ are the Young's modulus, density and transverse piezoelectric coefficient of the structural material, and h is the device thickness. Thus, FIG. 1c illustrates an X-component of the resonance plot for device C when it is driven nonlinearly. A lock-in amplifier locks on to the steepest point 118. When $V_{bias}$ 112 is applied the resonance, the plot shifts along the frequency axis, and the lock-in point varies in amplitude (120, 122). In this manner, signals are encoded as spectral amplitude variations at a specific frequency and can be transduced in real-time.

As equation (1) suggests, reducing the device 100A/100B thickness to nanoscale dimensions is important for maximizing sensitivity. In addition, sensitivity can be further enhanced by operating the resonator in the regime of nonlinear bistability (FIG. 1c), in which the slope η is increased. It can be emphasized that while non-piezoelectric NEMS devices can also transduce an applied bias through electrostatic coupling, their tuning action is nonlinear and thus less suitable for recovery of analog signals.[17-19]

The fundamental frequency of a NEMS resonator can be tailored through its length. An array of resonators of differing lengths can then be used to produce a nanomechanical Fourier transform, encoding signals in the time domain into spectral amplitude variations using the modulation scheme described. Optical readout techniques can subsequently monitor the oscillation amplitude of the resonators concurrently through a single transmission channel, provided the devices are spaced close together. Downstream demodulation of the optical signal can recover and uniquely identify the origin of a signal based on the rf actuation frequency. NEMS resonators can be operated at frequencies ranging from several megahertz to over one gigahertz,[20] suggesting thousands of different channels could be encoded onto a single output line.

Embodiments of the invention may provide a multiplexing technique, using laser interferometry[21] to monitor variations in transverse oscillation amplitude from the two closely spaced NEMS devices 100A and 100B depicted in FIG. 1a. The devices 100A and 100B have lengths of 9.0 and 8.5 μm, and resonate at 8.758 and 9.962 MHz, respectively. FIG. 1d illustrates a schematic of an experimental setup to demonstrate multiplexing through a nanomechanical transducer. All mechanical displacement is read out via a common optical transmission path. The beam from the laser 124 is focused to a diameter of ~10 μm, allowing concomitant observation of both resonant structures. The devices 100A and 100B are operated in vacuo 126 to maintain high quality factor and resonance frequency stability. Each device 100A and 100B is capacitively coupled to two signals: (i) the rf driving potential $V_{drive}$ 108, whose frequency corresponded to the region of highest X-quadrature slope 118 in FIG. 1c, and (ii) the bias signal 112 used to simulate the output of an analog electrical sensor. The single-channel photodetector 128 signal is demodulated using lock-in amplifiers 130A and 130B referred to $f_{drive}$ of each device.

FIG. 1e shows the demodulated signals transduced from devices 100A and 100B in accordance with one or more embodiments of the invention. Thus, the solid lines 132 in FIG. 1e illustrate the signals recovered from a multiplexed optical readout of devices 100A and 100B by means of the lock-in amplification (as illustrated in FIG. 1d). The original corresponding bias signal on each device is represented by the dashed lines 134. The small phase offset between 132 and 134 originates from the low-pass RC filter formed by the signal output impedance and large parasitic capacitance at the device wirebond contact region. The results displayed in FIG. 1e represent 450 averages.

Figure 4:
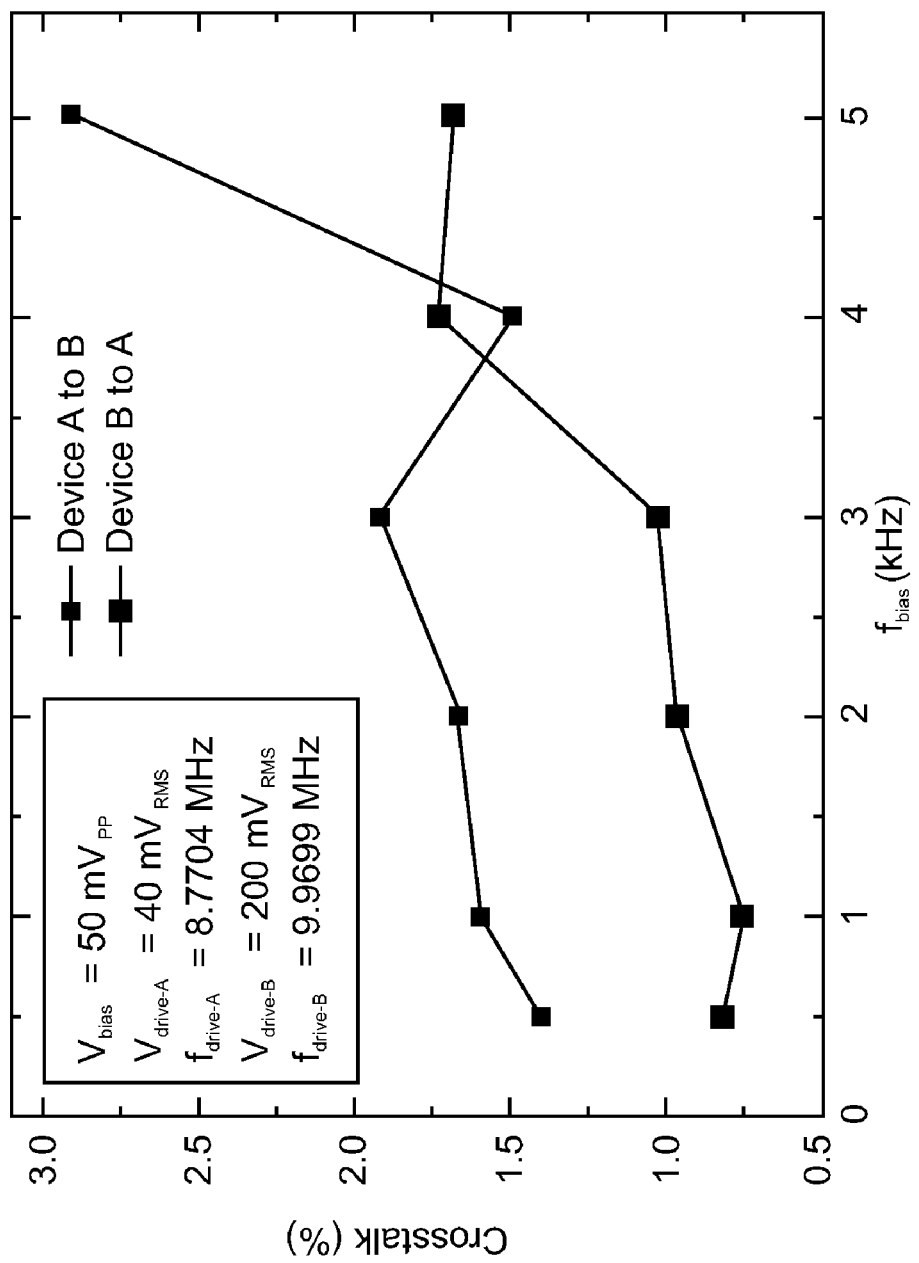
FIG. 4 illustrates the crosstalk versus the frequency between the devices of FIG. 1a in accordance with one or more embodiments of the invention.

Using the implementation illustrated in FIG. 1(d), the fine structure of the pulse applied to device 100A and the sinusoidally varying signal applied on device 100B can be closely reproduced. The cross-talk between signals applied on each device 100A and 100B did not exceed ~2% at 1 kHz, despite the close spacing of the beams. FIG. 4 illustrates the crosstalk versus the frequency between devices 100A and 100B in accordance with one or more embodiments of the invention. A 50 $mV_{pp}$ sinusoidal bias was applied to device 100A, and the demodulated photodetector signal was measured from the unbiased device 100B. Thus, any crosstalk manifests as a spurious signal on device 100B at the applied bias frequency. The percent crosstalk is calculated from the ratio of the spurious signal on 100B to the signal that is measured when a 50 mV$_{pp}$ bias is directly applied to 100B. A similar measurement can also be made with the bias signal applied to device 100B and crosstalk measured from device 100A.

Accordingly, using the above described embodiments, one can accurately track bias signals for tens of minutes without adjusting the rf driving potential parameters. Over longer time scales, a drift can be observed that was compensated by a single-shot manual recalibration of f$_{drive}$.

Figure 5:
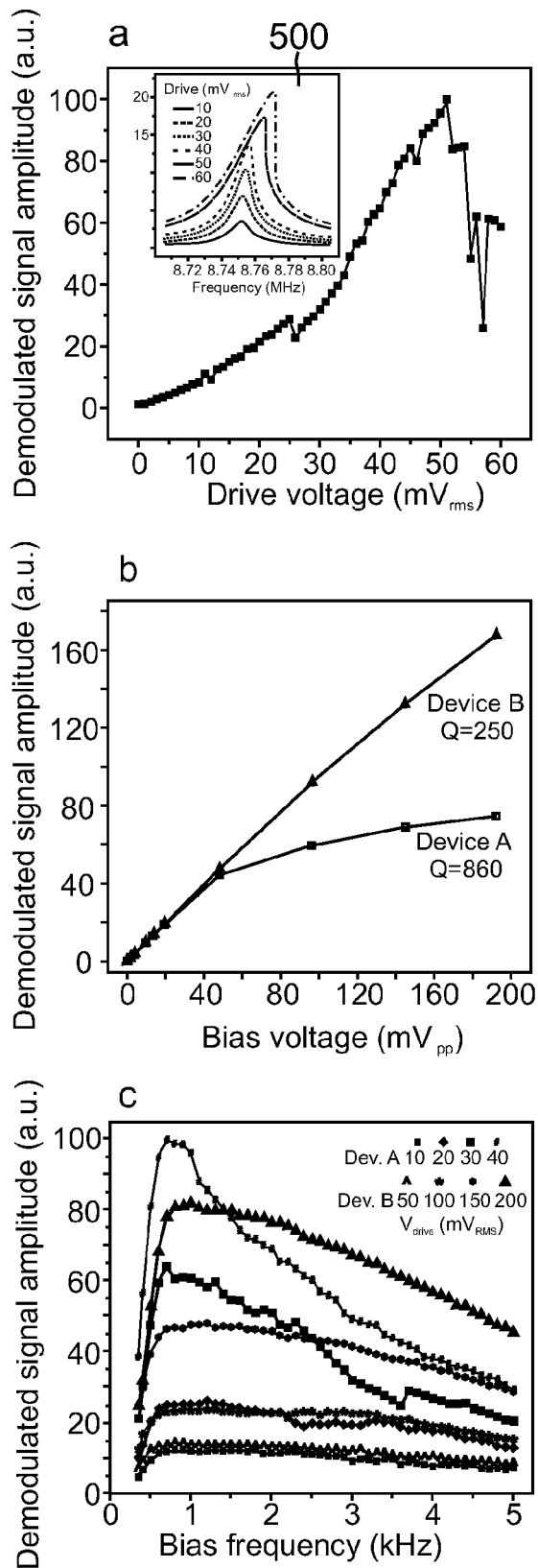
FIG. 5a illustrates a plot of the dependence of a transduced signal amplitude of a device of FIG. 1a on the rf drive voltage under a constant bias at 1 kHz in accordance with one or more embodiments of the invention.
FIG. 5b illustrates a nanomechanically transduced signal amplitude of a 1 kHz sinusoidal signal applied to the devices of FIG. 1a as a function of the applied bias amplitude in accordance with one or more embodiments of the invention.
FIG. 5c illustrates a bias frequency response of the devices of FIG. 1a at various driving amplitudes in the linear and nonlinear NEMS actuation regime in accordance with one or more embodiments of the invention.

FIG. 5a plots the dependence of the transduced signal amplitude of device 100A on the rf drive voltage under a constant bias at 1 kHz. The inset 500 shows resonance curves at representative values of V$_{drive}$. As illustrated, the system's response improves as a result of actuating the resonator in the regime of nonlinear bistability. Above a critical point corresponding to strong nonlinear drive the readout appears to become unstable, as suggested by the abrupt decrease in response. The optimal response for this particular device occurs just below the instability regime at V$_{drive}$≈50 mV$_{rms}$. The noise does not appreciably change below the instability (see FIG. 6) and thus confirms that the optimal signal-to-noise ratio (SNR) is achieved by actuating the NEMS devices at levels slightly lower than the critical point. Accordingly, FIG. 5a illustrates a device characterization with an enhancement of device 100A's transduced signal with an increasing rf drive amplitude. The bias signal amplitude and frequency are set to 30 mV$_{pp}$ and 1 kHz respectively. The inset shows resonance plots of the flexural oscillation amplitude at representative drive levels.

Figure 6:
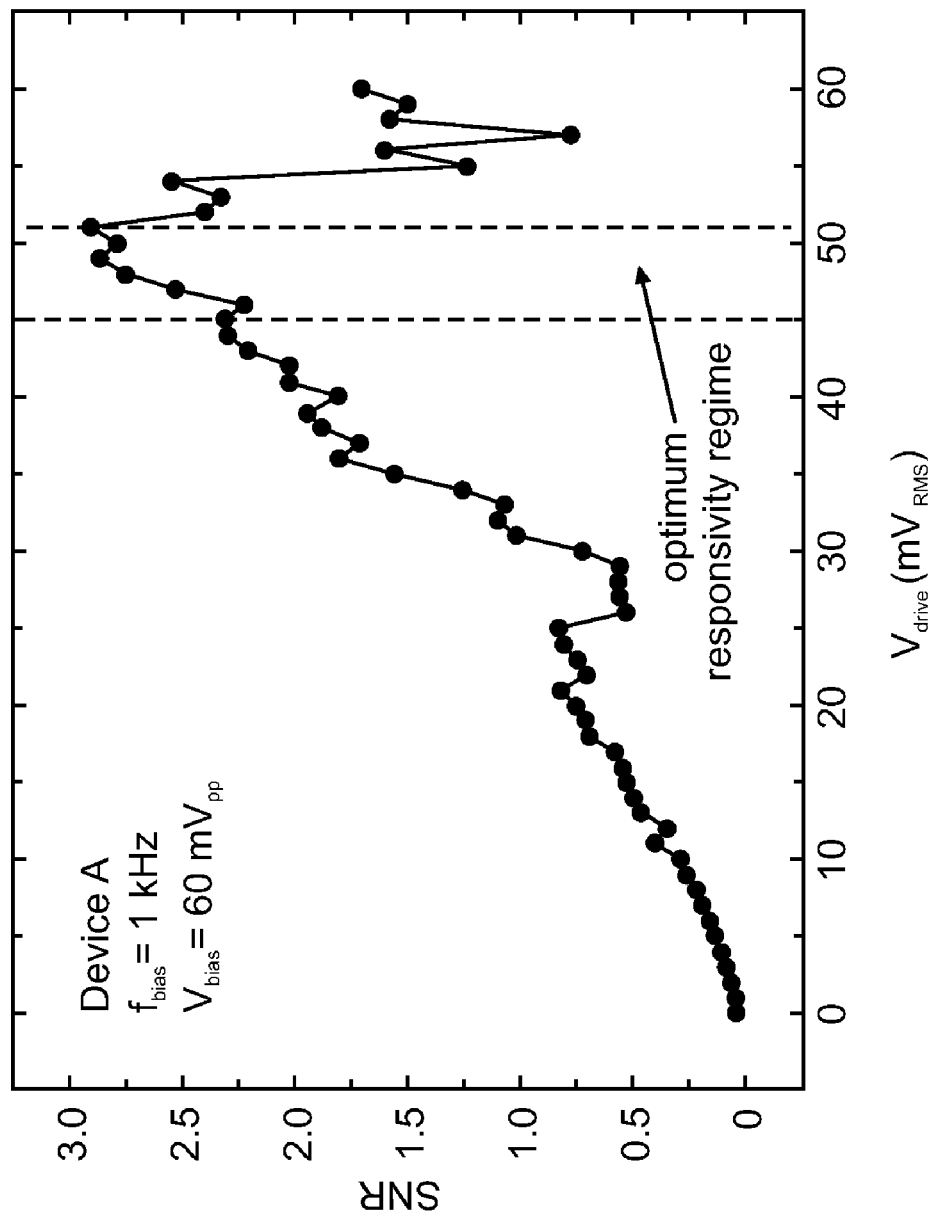
FIG. 6 illustrates a signal to noise ratio enhancement under nonlinear operation in accordance with one or more embodiments of the invention.

FIG. 6 illustrates the signal to noise ratio enhancement under nonlinear operation. The SNR for device 100A is plotted as a function of drive potential. The signal is measured as the root-mean-square amplitude of the demodulated NEMS response, during application of a 60 mV$_{pp}$, 1 kHz sinusoidal bias across the NEMS. RMS noise is measured by turning off the applied bias and recording background activity for ~100 seconds. Note that the regime of highest SNR occurs in the region of highest signal in FIG. 5a, which lies near the critical bistability point of nonlinear mechanical resonance.

By varying the bias amplitude under fixed V$_{drive}$, one can observe a linear response at low bias levels as illustrated in FIG. 5b. Note that the earlier onset of nonlinear response in device 100A compared to that of device 100B is due to its higher quality factor. Accordingly, FIG. 5b illustrates a nanomechanically transduced signal amplitude of a 1 kHz sinusoidal signal applied to devices 100A and 100B as a function of the applied bias amplitude. The actuation parameters are V$_{drive,A}$=40 mV$_{rms}$ and V$_{drive,B}$=200 mV$_{rms}$.

A characteristic of the nonlinear driving regime of the nanomechanical system is a greater attenuation of signal response at high bias frequency. FIG. 5c characterizes the frequency response for devices 100A and 100B under varying drive amplitude. For both devices 100A and 100B, the response curve remains flat at low V$_{drive}$, but becomes progressively biased toward lower frequencies as V$_{drive}$ approaches the critical point. The attenuation effect is more marked for the device with higher quality factor. Thus, FIG. 5c illustrates a bias frequency response of devices 100A and 100B at various driving amplitudes in the linear and nonlinear NEMS actuation regime. Note that the notch at f$_{bias}$<500 Hz is due to an applied high-pass filter and is not an intrinsic nanomechanical effect. V$_{bias}$ can be set to 30 mV$_{rms}$ for both devices 100A and 100B. For all plots, the demodulated signal amplitude was averaged 2,500 times.

The observations of FIGS. 5a-5c appear to be a manifestation of the ring-down time of the resonator, which is proportional to quality factor and is increased in nonlinearly excited systems. Such results closely agree with the theoretical prediction that the greatest voltage sensitivity of this system is achieved just below the critical point, but that this operating regime exhibits the longest ring-down effect and hence smallest bandwidth.[22] Electrical sensors requiring both high sensitivity and bandwidth nanomechanical transduction would therefore necessarily rely on the use of higher operating frequency NEMS resonators. As the system is linear, the original bias signals can be recovered through deconvolution with the frequency response characteristic of each device. The particular application of the system will determine the device quality factor specification and driving regime. This is due to the tradeoff in ultimate wiring density, signal bandwidth, sensitivity and SNR that arises from these factors. Greater quality factor increases the SNR and the number of channels that can be multiplexed in a given frequency band, but may limit the bandwidth and dynamic range of the transduced bias signal. Furthermore, stronger nonlinear drive increases SNR but impacts the bandwidth.

Some applications of sensors require measurement of low amplitude, low SNR bias signals. This challenge is particularly salient in the monitoring of electrophysiological activity in the brain using multisite extracellular electrode arrays. Such recordings are an invaluable method for studying functional properties of the intact brain from the microcircuit to systems level.[23] The enabling technology is an implantable neural probe that connects a grid of microscale electrodes to amplifying electronics via wires spanning the length of the probe. As the complexity of such neural interfaces increases, the primary size-determining factor of the devices becomes the wiring interconnects, and an arbitrary reduction of wire width is not necessarily a practical solution.[24]

Figure 7:
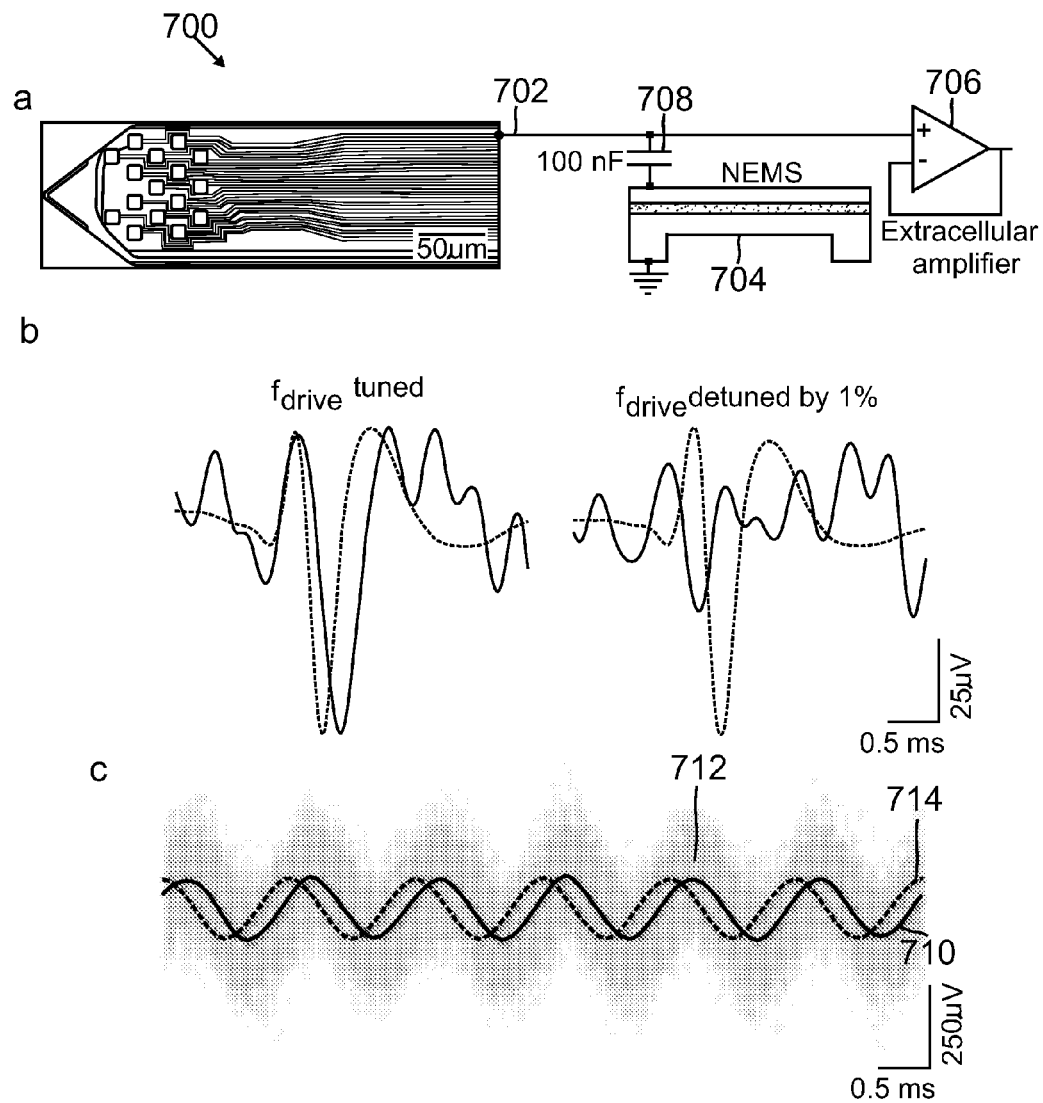

To overcome such wiring difficulties, embodiments of the invention examine the effectiveness of transducing extracellular action potentials via a NEMS-neural probe interface. FIGS. 7a-7c illustrate a nanomechanical transduction of extracelular action potentials in accordance with one or more embodiments of the invention. FIG. 7a illustrates a neural probe 700 that can be used in various experiments. A single channel 702 is connected in parallel to NEMS device C 704 (length, width, thickness)=(8, 0.8, 0.2) µm and an extracellular amplifier 706. The stand-alone resonator 704 can be coupled to a recording site on the probe 700 shown.[25]

A specific example of the use of the probe 700 of FIG. 7a provides for inserting the implantable section of the probe 700 into a locust thoracic ganglion induced to sustain rhythmically discharging neurons. The electrode is connected to the resonator 704 via a blocking capacitor 708, which prevents dc photoelectric charge generated at the GaAs device from coupling to the electrode. A parallel connection extends to an extracellular amplifier 706 for cross-validation of the nanomechanically transduced signal. Extracellular neuronal action potentials are identified from the amplifier 706 recording, allowing spike-triggered averages to be obtained on the synchronously collected measurements from the NEMS 704 and electronic amplifier 706.

The mean waveform of an 80 µV$_{pp}$ spike is depicted in FIG. 7b and is simultaneously observed at the demodulated output of the NEMS resonator 704. Accordingly, FIG. 7b illustrates the detection of extracellular action potentials in a locust ganglion preparation using the setup in FIG. 7a. Demodulated signals from the NEMS device 704 are shown as solid lines, and the corresponding signal recorded by the amplifier is indicated by dashed lines. Mechanical readout can be confirmed through the extinction of spike detection upon detuning the resonator 704 by 100 kHz (i.e., by verifying that the action potential is no longer measured if the resonator 704 is detuned by 1% from its fundamental frequency). Data is averaged over 5,000 spike-triggered events.

The transduced SNR is small when transducing signals as diminutive as those from extracellular microelectrodes. In order to achieve a measurable action potential waveform it may be necessary to average the NEMS signal from 5,000 spike events. The noise performance that may be achieved is 400 $\mu F_{RMS}$ referred to the microelectrode input (in the frequency band of 350 to 3,000 Hz), as shown by measurements displayed in FIG. 7c. In this regard, the neural probe 700 coupled to the NEMS device 704 can be used to detect an artificially generated signal in saline solution. The nanomechanical signal appears as a solid line 710 (250 averages). Individual, unaveraged NEMS traces are indicated by the shading 712. The averaged trace from the extracellular amplifier is a dashed line 714. The SNR of the transduced signal is ~1:1.

In contrast, conventional electronic amplifiers designed for electrophysiological recording have a noise floor approaching 1 $\mu V_{RMS}$.[26] Thus to approach the same performance level as the present invention, the SNR would need to be improved by at least two orders of magnitude. Although a number of engineering improvements could be made to the devices themselves to improve SNR,[27] it may be found that over 80% of the measured noise is not intrinsic to the devices 100A and 100B but originates in the external demodulation electronics (see FIGS. 8 and 9). There is thus opportunity for substantive improvement in performance.

Figure 8:
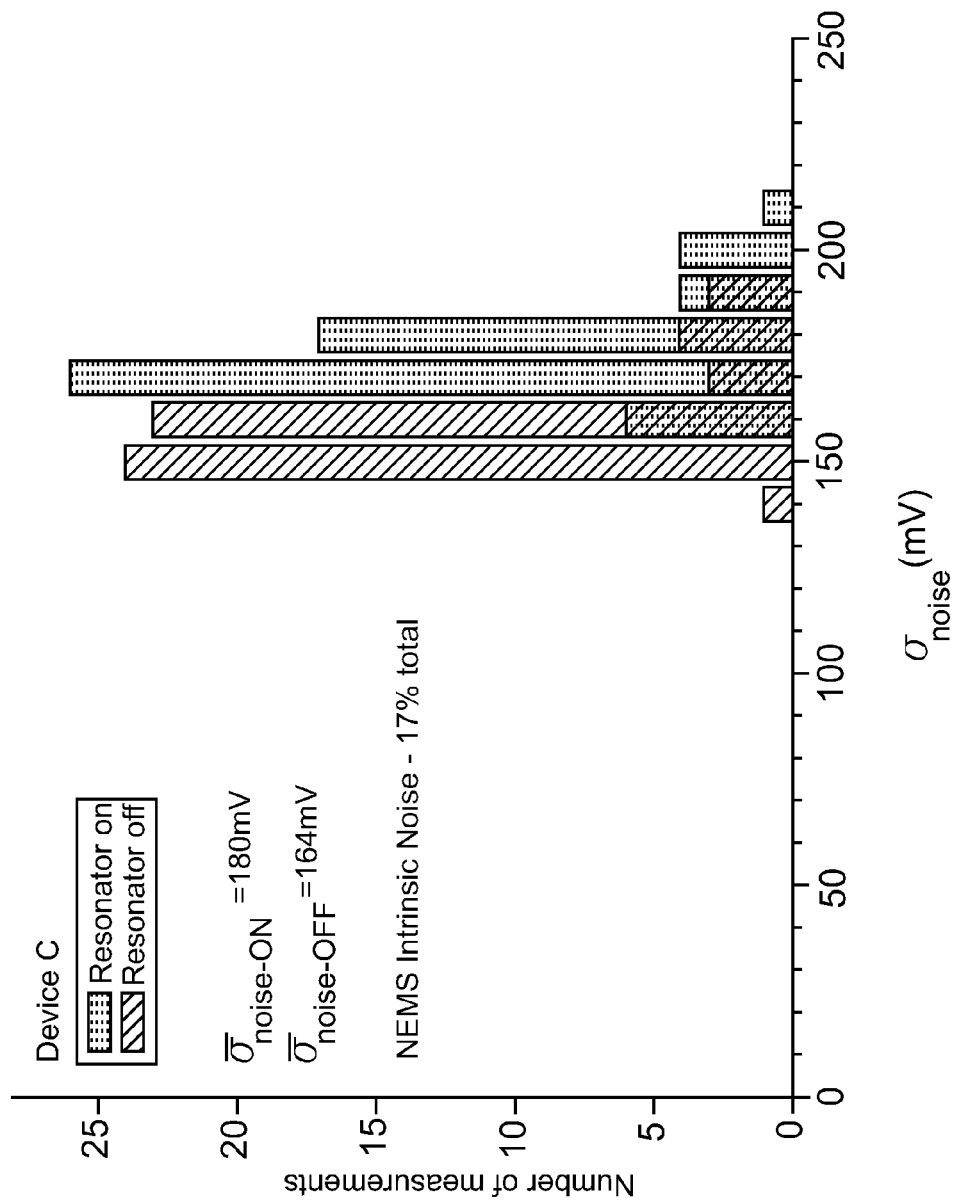
FIG. 8 illustrates the measurement of intrinsic noise where the capacitive input bias terminal of a NEMS device is grounded and background noise is measured from the optical signal both with the NEMS device tuned to resonance (left panel) and with the radiofrequency drive turned off (right panel) in accordance with one or more embodiments of the invention.

FIG. 8 illustrates the measurement of intrinsic noise where the capacitive input bias terminal of device C 704 is grounded and background noise is measured from the optical signal both with the device 704 tuned to resonance and with the radiofrequency drive turned off. In this regards, FIG. 8 illustrates a measurement where fifty-eight (58) recordings of 10 s duration were made under each condition and the noise standard deviation was determined in each case. The proportion of intrinsic noise contribution to the total noise was determined using the formula $(\sigma_{noise\text{-}ON}^2 - \sigma_{noise\text{-}OFF}^2)/\sigma_{noise\text{-}ON}^2$. The drive amplitude was 40 $mV_{RMS}$ during device actuation. Data was filtered using an 8-pole Butterworth filter in the pass band of 300 to 10,000 Hz. These results suggest that over 80% of the measured noise was not intrinsic to the device itself, but originated elsewhere in the system such as the demodulation electronics.

Figure 9:
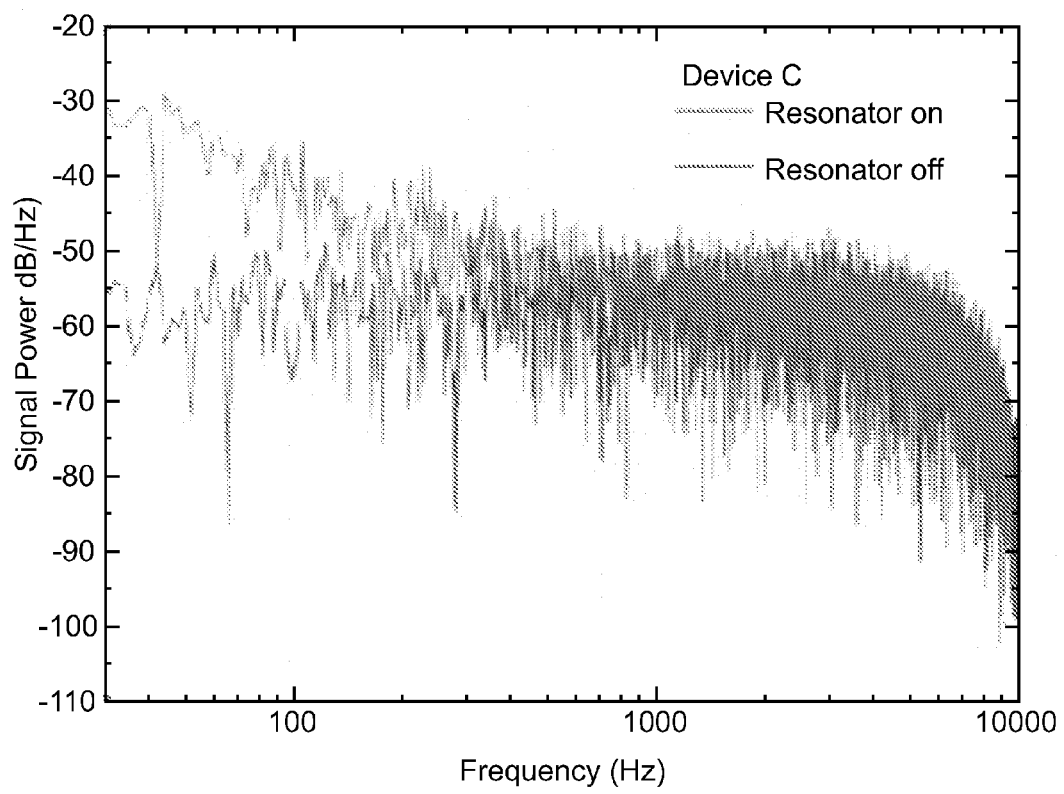
FIG. 9 illustrates the noise power spectrum (based on a spectral analysis of the noise data from FIG. 8) in accordance with one or more embodiments of the invention.

FIG. 9 illustrates the noise power spectrum (based on a spectral analysis of the noise data from FIG. 8) in accordance with one or more embodiments of the invention. Data for each curve was acquired over a period of ten (10) minutes.

In one or more embodiments of the present invention, two physical wires may be required in addition to the optical interconnect for communication with the external environment; a ground terminal and a path carrying the multi-frequency AC drive generated externally. However, on-chip waveguide fabrication and evanescent wave optical detection schemes[28,29] may be integrated with piezoelectric NEMS. Such an interface may enable the use of miniature nanoscale integrated sensors that can be positioned at any place in the human body, and be used to extract vast amounts of information in real-time and with single-cell fidelity.

Detailed Description of Materials and Methods

The description in this section sets forth details regarding the materials and methods used to wire nanoscale sensors with nanomechanical resonators in accordance with one or more embodiments of the invention.

The heterostructure used to fabricate the piezoelectric resonators may include (bottom to top, with doping concentration in $cm^{-3}$ in parentheses): a highly p-doped GaAs substrate, 550 nm p-$Al_{0.8}Ga_{0.2}As$ ($10^{18}$) sacrificial layer, followed by the pin structure of 100 nm n-GaAs ($10^{19}$), 50 nm i-GaAs (~$5 \times 10^{15}$), and 50 nm p-GaAs ($10^{18}$). The fabrication method is described in [3]. Alternatively, different piezoelectric materials may be used such as Aluminum Nitride. In this regard, embodiments of the invention may be implemented using any type of piezoelectric materials. All NEMS can be aligned along the [−110] axis, for which the transverse piezoelectric constant, $d_{31} \leq 1.4 \times 10^{-12}$ m/V. Alternatively, other/different axes could be used to align the NEMS devices.

The optical interferometry detection scheme (used for measurement) may employ an infrared laser diode source (904 nm, 30 mW, Thor Labs) whose wavelength exceeded the photonic band gap wavelength of GaAs in order to minimize heating and surface charge excitation effects. Despite this precaution, some dc photoelectric effects may be observed, which can necessitate the placement of a 100 nF dc blocking capacitor between the NEMS device and voltage bias source (e.g., as illustrated in FIG. 7a). A silicon pin photodetector may be employed for detection (New Focus Inc., model 1801™). Lock-in measurements may be made with Stanford Research Systems RF amplifiers model SR844™. All data may be acquired at a sampling rate of 30 kHz. To improve SNR, an 8-pole high-pass Butterworth filter may be applied to the acquired data; $f_{cutoff}$ may be set to 300 Hz for the data in FIG. 1e and FIG. 5. Moreover a low-pass filter may be applied to highlight the typical bandwidth of an analog sensor ($f_{cutoff}$=10,000 Hz). Identical filter settings can always be used on both the nanomechanically transduced and original bias voltage signals.

Voltage and displacement calibration may also be conducted. The optimal value for $f_{drive}$ (see FIG. 1c) can be determined by applying a 1 kHz sinusoidal bias 112 of known amplitude across the NEMS device 102 terminals (all potentials are with respect to the n-doped terminal), and manually sweeping the drive frequency until the largest demodulated signal is observed on an oscilloscope. The demodulated signal amplitude could then be calibrated to the known value of $V_{bias}$ 112. The nanomechanical displacement in the inset of FIG. 5a can be estimated from the expression for critical amplitude at the onset of nonlinear bistability, derived in reference [30].

In view of the above, embodiments of the invention may be utilized in a neural probe as illustrated in FIG. 7a. The following information describes the creation of the probe 700 illustrated in FIG. 7a. The microelectrode array may be fabricated from 25 µm thick silicon substrates with 2 µm thermally grown $SiO_2$ serving as the bottom insulation layer (as described in U.S. patent application Ser. No. 12/335,847 which is incorporated by reference herein). Gold electrodes and interconnects may be deposited in a thermal evaporator, followed by deposition of a conformal film of parylene C. The parylene C is selectively etched in oxygen plasma to expose the square recording sites on the tip, whilst keeping the interconnects insulated. Next the oxide and silicon layers are etched, and the device is flip-chip bonded onto a printed circuit board.[25] The recording site impedance is reduced via gold electrodeposition to ~30 kΩ at 1 kHz, in order to avoid RC filtering effects from the large (~100 pF) parasitic capacitance between the bias and reference terminal. The majority of this capacitance originates at the wirebond contact region for the NEMS device.

Once the probe 700 is created, it may be used/combined with a NEMS device to measure neural activity. A thoracic ganglion is prepared under the protocol described in reference [31], and provided stable neuronal recordings for several hours. The isolated ganglia is bathed in 100 µM pilocarpine solution to elicit rhythmic firing of motor neurons. An Ag/AgCl electrode serves as the electrical potential reference. The assembled probe 700 is mounted onto a micromanipulator and inserted into the thoracic ganglion until a stable spiking unit is located. After data acquisition, the signal from the extracellular electronic amplifier 706 (e.g., Intan Technologies, RHA1016™) is filtered in the pass band of 400 to 4,000 Hz and fed to a spike sorting routine written for Matlab™.[32] Spikes are identified based on an amplitude threshold method, and clustered according to the Euclidean distance between their waveforms. After identifying a putative single unit's spike times, the spike times are used to extract the waveforms from the concurrently recorded NEMS signal from the photodetector. 5,000 waveforms can be superposed and averaged to yield the results in FIG. 7b. Before generating FIG. 7b, the original data may be re-filtered to reduce noise artifacts, in the pass band of 300 to 2,500 Hz. The action potential signals are attenuated and eventually abolished upon retracting the neural probe 700 from its nominal recording location, confirming the neuronal origin of the spikes. Measurements for the plot in FIG. 7c can be generated by passing a 400 $\mu V_{pp}$ 1 kHz sinusoidal bias signal into a saline bath in which the probe is immersed. The bias signal is applied between two Ag/AgCl electrodes, one of which is connected to the NEMS and amplifier reference. Recorded signals are filtered from 350 to 3,000 Hz, and segments spanning a few milliseconds were aligned and averaged.

Application of Nanomechanical Wiring to Large Scale Electrophysiology

One or more embodiments of the invention provide the ability to use wiring sensors via nanomechanical resonators to monitor electrophysiological activity across large areas of the brain with high spatial resolution.[23] As illustrated in FIG. 7a, in a typical neural probe 700 interface, an array of microscale electrodes is positioned along an implantable shaft. These electrodes measure small extracellular potentials, on the order of tens to hundreds of microvolts. As long as the electrodes are sufficiently small a neural probe can provide information on the firing activity of several single neurons in parallel.

The development of more complex neural probes, that can monitor larger areas of the brain and at higher spatial resolution, can provide novel opportunities in the study of the brain, but requires a tradeoff between two important sensor design considerations. On one hand, it is desirable to maximize the area covered by the array by employing several hundreds to thousands of closely spaced, individually addressable recording sites. On the other hand, there is a need to miniaturize the neural probe in order to minimize damage to the surrounding tissue. As with other classes of sensors, as the number of recording channels is scaled up, the primary size-determining factor becomes the interconnecting wiring between the electrodes and macroscopic world (i.e., amplifiers and computer interface). Moreover, a reduction in wiring width and spacing may not be an effective solution to this problem because the high impedance of these wires would exacerbate signal crosstalk and attenuation.[24]

Figure 10:
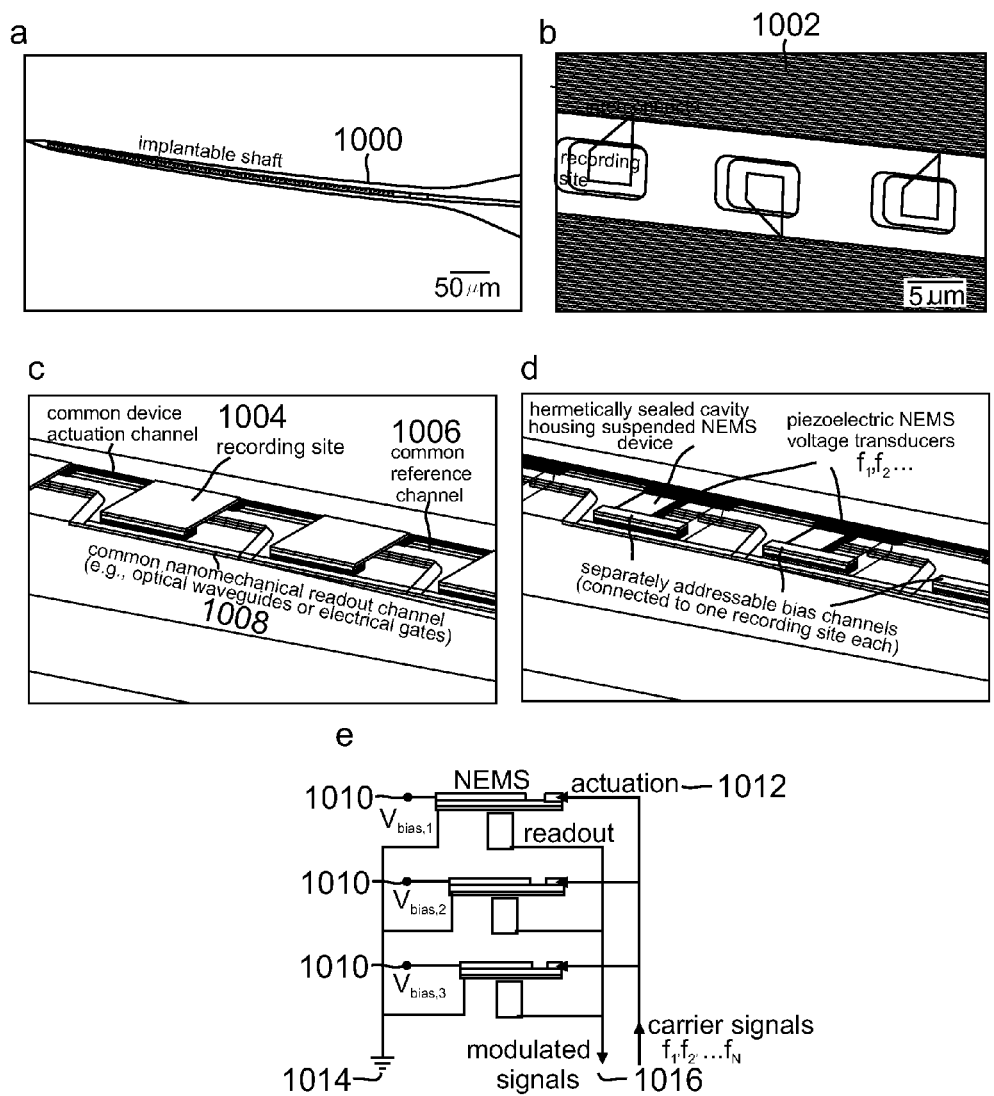
FIG. 10a illustrates an SEM image of a silicon neural probe containing 64 recording sites in accordance with one or more embodiments of the invention.
FIG. 10b illustrates a close-up of the probe of FIG. 10a showing that a significant portion of the shaft width can be occupied by wiring in accordance with one or more embodiments of the invention.
FIG. 10c illustrates the elimination of wiring using electrical potentials to modulate a frequency-tunable element such as a piezoelectric NEMS device in accordance with one or more embodiments of the invention.
FIG. 10d is a diagram illustrating the conceptual drawing of FIG. 10c where the recording electrodes have been removed to reveal the cavity that houses the NEMS devices in accordance with one or more embodiments of the invention.
FIG. 10e illustrates a simplified schematic representation of the multiplexed signal transduction scheme in accordance with one or more embodiments of the invention.

Accordingly, a technique allowing multiplexing of signals in the immediate vicinity of the recording sites can circumvent the need for using multiple long interconnections and enable development of much higher density and less invasive neural interfaces. A new type of implantable neural probe containing a planar microelectrode array can be fabricated with the voltage-transducing elements multiplexed onto a single output as illustrated in FIG. 10. Accordingly, FIGS. 10a-10e illustrate a conventional wiring scheme and nanomechanical wiring scheme for neural probes in accordance with one or more embodiments of the invention.

FIG. 10a illustrates a SEM image of a silicon neural probe 1000 containing 64 recording sites. FIG. 10b illustrates a close-up of the probe 100 showing that a significant portion of the shaft width can be occupied by wiring 1002. The wires 1002 shown in FIG. 10b are 500 nm wide and have spacing of 500 nm. The electrical potential at each electrode can be altered by local extracellular fields in the brain. However, rather than routing signals from each recording site with a wire spanning the length of the probe (as in FIGS. 10a and 10b), each channel can be locally coupled to a low power piezoelectric NEMS device that resonates at a unique frequency.

FIG. 10c shows that most of the wires 1002 can be eliminated if electrical potentials modulated a frequency-tunable element such as a piezoelectric NEMS device 1004, that would enable mixing of multiple bias channels 1006 on a common readout channel 1008. In FIG. 10c, the voltage-sensitive, piezoelectrically coupled resonator (not shown) lies directly beneath the rectangular recording site electrode 1004.

The nanomechanical components 1004 can be fabricated directly beneath the corresponding recording site and contained in a hermetically sealed vacuum environment. FIG. 10d is a diagram illustrating the conceptual drawing of FIG. 10c where the recording electrodes have been removed to reveal the cavity that houses the NEMS devices 1004. Nanomechanical vibrations do not exceed a few nanometers in amplitude, thus the cavity need not be much thicker than the NEMS device 1004 thickness. Each NEMS resonator 1004 has a different fundamental frequency and is connected to a separately addressable recording site. In addition, all resonators share a common actuation, reference and displacement readout channel 1008. Nanomechanical displacements could be measured via optical or electrical means.

FIG. 10e illustrates a simplified schematic representation of the multiplexed signal transduction scheme in accordance with one or more embodiments of the invention. The operation of a large set of parallel-connected NEMS devices 1004 would require four connections per resonator: the locally connected bias voltage 1010 from the extracellular electrode, plus a common multi-frequency drive actuation path 1012, ground terminal 1014, and nanomechanical readout path 1016. Approximately 1,000 data channels may be transmitted off the neural probe 1000 in this parallel manner, assuming an operating NEMS frequency band of 10 MHz to 250 MHz, a Q of 2,000 and nearest neighbor frequency separation of $3(f_i+f_{i+1})/Q$. The number of channels can be even higher if the bandwidth is expanded to include microwave frequencies.

Further Applications of the NEMS Transduction Method

Piezoelectric NEMS transducers can also be used to monitor electrophysiological activity from heart muscles. This could be achieved by coupling the NEMS device to a voltage sensing element such as a metal microelectrode, a semiconductor nanowire, or a carbon nanotube. In this manner, the electrical potential at multiple points of the heart could be monitored in real time via an array of sensors coupled to a single data output path. In addition, the NEMS transduction method can be applied to transduce signals from a large array of voltage-sensitive biochemical sensors.

Accordingly, embodiments of the invention are not intended to be limited to neural based devices but may extend to any type of voltage-sensitive biomechanical sensors. Embodiments of the invention are not intended to be limited in scope by the specific embodiments described above but by the claims of this application.

Logical Flow

Figure 11:
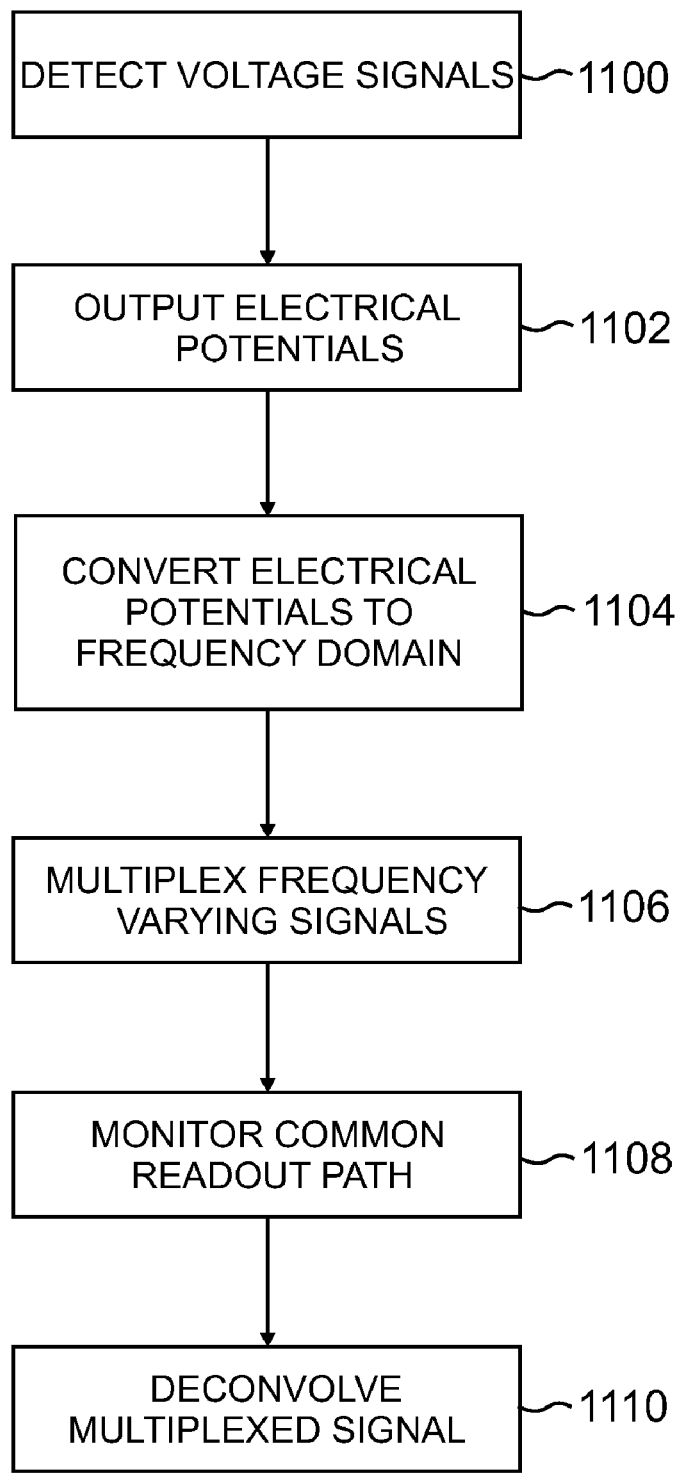
FIG. 11 illustrates the logical flow for wiring a voltage sensitive device to a nanoelectromechanical system (NEMS) resonator in accordance with one or more embodiments of the invention.

FIG. 11 illustrates the logical flow for wiring a voltage sensitive device to a nanoelectromechanical system (NEMS) resonator. At step 1100, a voltage sensitive device is used to detect one or more voltage signals. In this regard, the voltage sensitive device may detect the electrical potential change on a sensor.

At step 1102, the voltage sensitive device outputs one or more electrical potentials (based on the one or more voltage signals) in real-time. The voltage sensitive device is configured to detect and output voltage signals as small as a microvolt (and the NEMS resonator can process/convert such microvolt size electrical potentials in real-time). Such an output can be viewed as the application of the detected electrical potential shift/change onto a voltage-transducing device (e.g., NEMS).

At step 1104, the electrical potentials are converted, in real-time, to a frequency domain using an array of piezoelectric NEMS resonators. To perform the conversion/transduction the voltage sensitive device is communicatively coupled to the array of piezoelectric NEMS resonators. Each resonator in the array is tuned to a unique frequency and the array converts each output electrical potential to a corresponding frequency varying signal. In one or more embodiments, the unique frequency that each NEMS resonator is tuned to is in the range of several megahertz to over one gigahertz thereby increasing a number of the frequency varying signals that can be/are multiplexed into the common readout path. Further, the output signal from each resonator varies in linear proportion to the resonator's corresponding frequency variation arising from the applied electrical potential. Such a conversion/transduction may be based on or produces a nanomechanical Fourier transform that is mediated by the piezoelectric NEMS resonators. Accordingly, the time-varying electrical potentials are converted into resonance frequency-modulating signals.

To perform the conversion, each resonator has a resonant member that can take a variety of forms. As described above, the NEMS device may consist of/comprise a movable/resonant member that includes a region of low conductivity over which an electric field is developed. The width of the region (referred to as region width) is within a factor of ten (10) of a thickness of the NEMS device. Such a region of low conductivity may be a depletion layer. In addition, the region may be formed between a junction that incorporates piezoelectric material. In one or more embodiments, such a junction may be formed by differently doped semiconductors. For example, the junction may be a PIN diode, a p-type/n-type junction, a p-n-p type junction, or a n-p-n type junction.

An exemplary resonator is that of a semiconductor p-type/intrinsic/n-type (PIN) diode. A charge depleted high resistance region or depletion region in the middle of the PIN diode forms a piezoelectrically active layer. Each piezoelectric NEMS resonator is tuned to a unique fundamental frequency by being fabricated at slightly different length. Further, the fundamental frequency of a doubly clamped resonator can depends on its length. The AC signal (which consists of one or more of the output electrical potentials from the voltage sensitive device) is applied across the PIN diode to produce a strain on the piezoelectrically active layer. The strain results in an actuation or mechanical resonance of the resonant member at or near its resonance frequency. In this regard, the vibrational amplitude of the resonator will change as it is actuated from the electrical potential received. With each resonator tuned to a different frequency, at least one of the resonators in the array should be actuated by the electrical potential received.

At step 1106, the frequency varying signals are multiplexed together into a single readout signal path.

At step 1108, the multiplexed frequency varying signals are continuously monitored to determine variations in vibrational amplitude of the signals.

At step 1110, the multiplexed varying signals are deconvolved to recover and uniquely identify the output electrical signals (e.g., based on the variations from the monitoring).

As described above, the voltage sensitive device may be an implantable neural probe that contains a grid of recording site electrodes. Each recording site electrode is communicatively coupled to one of the piezoelectric NEMS resonators.

Figure 12:
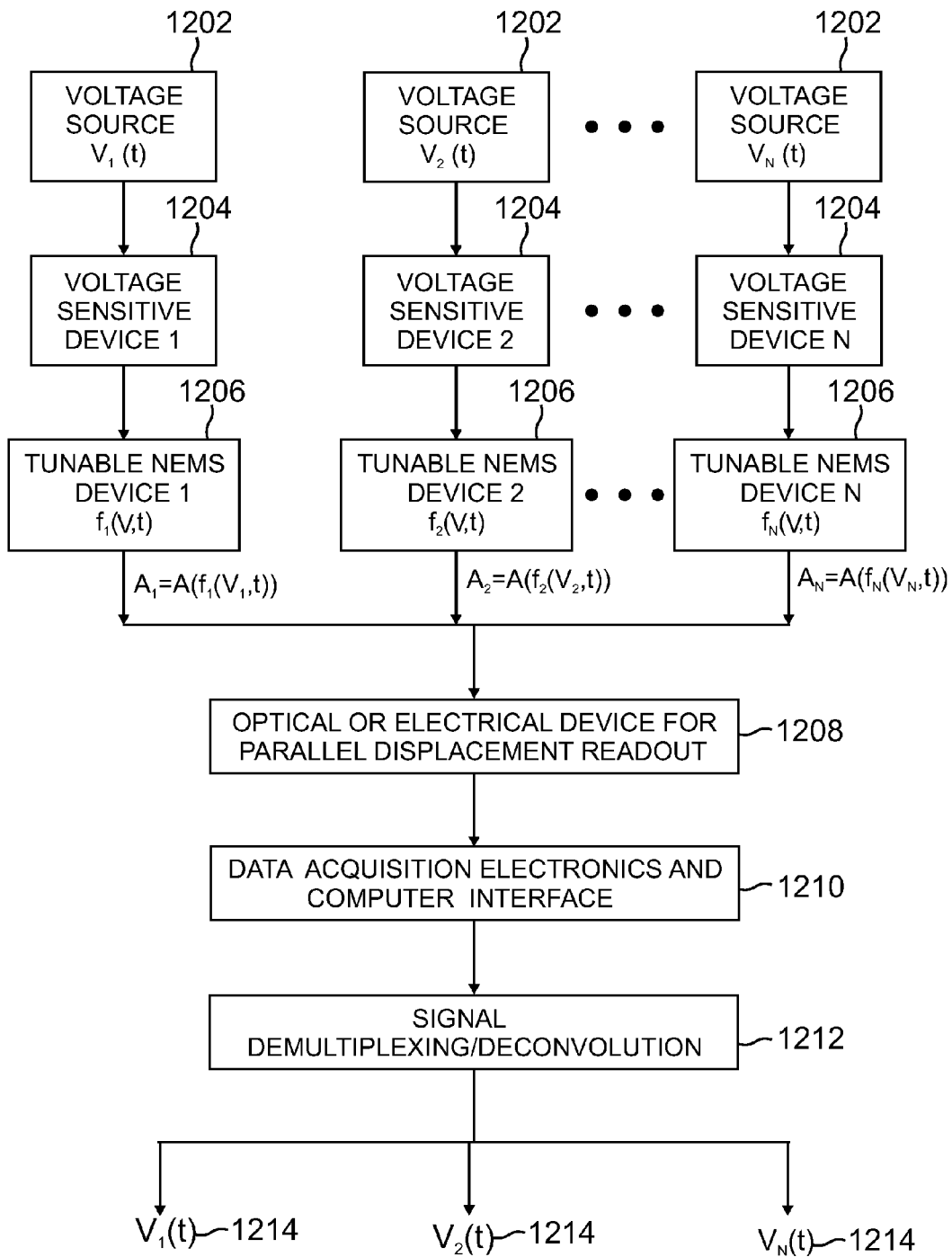
FIG. 12 illustrates the logical flow for wiring multiple voltage sensitive devices to the array of NEMS resonators in accordance with one or more embodiments of the invention.

FIG. 12 illustrates the logical flow for wiring multiple voltage sensitive devices to the array of NEMS resonators in accordance with one or more embodiments of the invention. As illustrated the various voltage sources $V_1(t)$-$V_N(t)$ 1202 are used to output electrical potentials. The output electrical potentials or the change in electrical potential is detected using voltage sensitive devices 1-N 1204. The voltage sensitive devices 1204 pass the signals onto the tunable NEMS devices $f_1(V,t)$-$f_N(V,t)$ 1206. In this regard the electrical potential signals received are in the time-varying domain (i.e., are volts (V) in units of time (t)).

The signals are processed and converted by the tunable NEMS devices 1206 into resonance frequency-modulating signals. In this regard, the amplitude of the signals can be measured (as $A_1 = A(f_1(V_1,t))$, $A_2 = A(f_2(V_2,t))$ ... $A_N = A(f_N(V_N,t))$).

The frequency varying signals are readout in parallel by an optical or electrical device 1208 that multiplexes the signals and transmits the multiplexed signal on a single output path (e.g., $A_1 + A_2 + \ldots A_N$). The multiplexed signal may then be stored, acquired, displayed, etc. using data acquisition, electronics and computer interface 1210.

The multiplexed signal can then be demultiplexed or deconvolved at 1212 into the original voltage signals (e.g., $V_1(t), V_2(t), \ldots V_N(t)$) (viewed in FIG. 12 as 1214).

CONCLUSION

This concludes the description of the preferred embodiment of the invention. The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

REFERENCES

[1] Joachim, C.; Gimzewski, J. K.; *Chem. Phys. Lett.* 1997, 265, 353-357.

[2] Bachtold, A.; Hadley, P.; Nakanishi, T.; Dekker, C.; *Science* 2001, 294, 1317-1320.

[3] Kong, J.; Franklin, N. R.; Zhou, C. W.; Chapline, M. G.; Peng, S.; Cho, K. J.; Dai, H. J.; *Science* 2000, 287, 622-625.

[4] Cui, Y.; Wei, Q.; Park, H.; Lieber, C. M.; *Science* 2001, 293, 1289-1292.

[5] Ekinci, K. L.; Huang, X. M. H.; Roukes, M. L.; *Appl. Phys. Lett.* 2004, 84, 4469-4471.

[6] Zhong, Z.; Wang, D.; Cui, Y.; Bockrath, M. W.; Lieber, C. M.; *Science* 2003, 302, 1377-1379.

[7] Beckman, R.; Johnston-Halperin, E.; Luo, Y.; Green, J. E.; Heath, J. R.; *Science* 2005, 310, 465-468.

[8] Wang, Z. L.; Song, J.; *Science* 2006, 312, 242-246.
[9] Walt, D. R.; *Nature Mater.* 2002, 1, 17-18.
[10] Zheng, G.; Patolsky, F.; Cui, Y.; Wang, W. U.; Lieber, C. M.; *Nature Biotechnol.* 2005, 23, 1294-1301.
[11] Patolksy, F.; Timko, B. P.; Yu, G. H.; Fang, Y.; Greytak, A. B.; Zheng, G. F.; Lieber, C. M.; *Science* 2006, 313, 1100-1104.
[12] Feynman, R. P.; *Feynman Lectures on Computation.* 1996. Addison-Wesley, Reading, Mass.
[13] Rabbitt, R. D.; Ayliffe, H. E.; Christensen, D.; Pamarthy, K.; Durney, C.; Clifford, S.; Brownell, W. E.; *Biophys. J.* 2005, 88, 2257-2265.
[14] Denk, W.; Webb, W. W.; *Phys. Rev. Lett.* 1989, 63, 207-210.
[15] Pumphrey, R. J.; Gold, T.; *Proc. R. Soc. London Ser. B.* 1948, 135, 462-491.
[16] Masmanidis, S. C.; Karabalin, R. B.; De Vlaminck, I.; Borghs, G.; Freeman, M. R.; Roukes, M. L.; *Science* 2007, 317, 780-783.
[17] Cleland, A. N.; Roukes, M. L.; *Nature* 1998, 392, 160-162.
[18] Truitt, P. A.; Hertzberger, J. B.; Huang, C. C.; Ekinci, K. L.; Schwab, K. C.; *Nano Lett.* 2007, 7, 120-126.
[19] Unterreithmeier, Q. P.; Weig, E. M.; Kotthaus, J. P.; *Nature* 2009, 458, 1001-1004.
[20] Huang, X. M. H.; Feng, X. L.; Zorman, C. A.; Mehregany, M.; Roukes, M. L.; *New J. Phys.* 2005, 7, 247.
[21] Can, D. W.; Craighead, H. G.; *J. Vac. Sci. Technol. B* 1997, 15, 2760-2763.
[22] Buks, E.; Yurke, B.; *Phys. Rev. E* 2006, 74, 046619.
[23] Buzsáki, G.; *Nature Neurosci.* 2004, 7, 446-451.
[24] Najafi, K.; Ji, J.; Wise, K. D.; *IEEE Trans. Biomed. Eng.* 1990, 37, 1-11.
[25] Du, J.; Riedel-Kruse, I. H.; Nawroth, J. C.; Roukes, M. L.; Laurent, G.; Masmanidis, S. C.; High-resolution three-dimensional recording of neuronal activity with microfabricated electrode arrays, *J. Neurophsyiol.* 2009, 101, 1671-1678.
[26] Harrison, R. R.; Charles, C. A.; *IEEE J. Solid-State Circuits* 2003, 38, 958-965.
[27] Reduction of parasitic capacitance through miniaturization of device contacts would ameliorate signal attenuation effects. Quality factor enhancement and the use of more strongly coupled and stiff piezoelectric materials such as AlN would improve voltage responsivity. An array of identical NEMS devices serving each channel would multiply the signal.
[28] Li, M.; Pernice, W. H. P.; Xiong, C.; Baehr-Jones, T.; Hochberg, M.; Tang, H. X.; *Nature* 2008, 456, 480-484.
[29] De Vlaminck, I.; Roels, J.; Taillaert, D.; Van Thourhout, D.; Baets, R.; Lagae, L.; Borghs, G.; *Appl. Phys. Lett.* 2007, 90, 233116.
[30] Tilmans, H. A. C.; Elwenspoek, M.; Fluitman, J. H. J.; *Sens. Actuat. A* 1992, 30, 35-53.
[31] Ryckebusch, S.; Laurent, G.; *J. Neurophysiol.* 1994, 72, 2771-2785.
[32] Rutishauser, U.; Schuman, E. M.; Mamelak, A. N.; *J. Neurosci. Meth.* 2006, 154, 204-224.

What is claimed is:

1. A system for wiring a voltage sensitive device to a nanoelectromechanical system (NEMS) resonator comprising:
   (a) a voltage sensitive device configured to detect one or more voltage signals and output one or more electrical potentials in real-time;
   (b) an array of piezoelectric NEMS resonators, wherein:
      (i) each piezoelectric NEMS resonator in the array is tuned to a unique frequency;
      (ii) the array of NEMS resonators is connected to the voltage sensitive device and is configured to perform the following steps in real-time:
         (1) receive the one or more output electrical potentials from the voltage sensitive device;
         (2) convert, using one or more of the tuned NEMS resonators, each output electrical potential to a corresponding resonance frequency varying signal, wherein an output signal from each NEMS resonator varies in linear proportion to the resonator's corresponding frequency variation arising from the output electrical potential applied to the NEMS resonator;
      (iii) the frequency varying signals are multiplexed together into a single readout signal path;
   (c) a monitoring system connected to the readout signal path and configured to continuously monitor the multiplexed frequency varying signals in the common readout path to determine variations in vibrational amplitude of the frequency varying signals; and
   (d) a demodulation device connected to the readout signal path and configured to deconvolve the multiplexed frequency varying signals in the common readout path to recover and uniquely identify the output electrical potential.

2. The system of claim 1, wherein:
each piezoelectric NEMS resonator comprises a resonant member including a semiconductor p-type/intrinsic/n-type (PIN) diode;
a charge depleted high resistance region or depletion region in a middle of the PIN diode forms a piezoelectrically active layer;
each piezoelectric NEMS resonator is prescribed a unique fundamental frequency by designing each resonant member to have a different length;
an AC signal is applied across an electrical terminals of the resonant member to produce a strain on the piezoelectrically active layer;
the AC signal comprises the one or more output electrical potentials from the voltage sensitive device; and
said strain results in an actuation or mechanical resonance of the resonant member at or near its resonance frequency.

3. The system of claim 1, wherein:
each piezoelectric NEMS resonator comprises:
a movable member including a region of low conductivity over which an electric field is developed wherein a region width is within a factor of ten (10) of a thickness of the NEMS resonator;
wherein the region is formed between a junction that incorporates piezoelectric material, wherein applying a first voltage across the region alters a width of an active portion of the region thereby adjusting a movement of the movable member induced by the output electrical potentials;
wherein the output electrical potentials are applied across the region to produce a strain on the active portion of the region, wherein said strain results in a defined movement of the movable member.

4. The system of claim 1, wherein:
the voltage sensitive device is configured to detect and output a microvolt; and
the array of piezoelectric NEMS resonators convert the microvolt size electrical potential to the corresponding frequency varying signal.

5. The system of claim 1, wherein the array of NEMS resonators are used to produce a nanomechanical Fourier transform.

6. The system of claim 1, wherein the unique frequency that each NEMS resonator is tuned to is in the range of several megahertz to over one gigahertz thereby increasing a number of the frequency varying signals that are multiplexed into the common readout path.

7. The system of claim 1, wherein:
the voltage sensitive device comprises an implantable neural probe comprising a grid of recording site electrodes; and
each recording site electrode is communicatively coupled to one of the piezoelectric NEMS resonators.

8. A method for wiring a voltage sensitive device to a nanoelectromechanical system (NEMS) resonator comprising:
(a) detecting, using a voltage sensitive device, one or more voltage signals;
(b) outputting, using the voltage sensitive device, one or more electrical potentials in real-time;
(c) converting, in real-time, using an array of piezoelectric NEMS resonators, the electrical potentials to a frequency domain, wherein:
  (i) the voltage sensitive device is communicatively coupled to the array of piezoelectric NEMS resonators;
  (ii) each piezoelectric NEMS resonator in the array is tuned to a unique frequency;
  (iii) the array of NEMS resonators convert, using one or more of the tuned NEMS resonators, each output electrical potential to a corresponding resonance frequency varying signal, wherein an output signal from each NEMS resonator varies in linear proportion to the resonator's corresponding frequency variation arising from the output electrical potential applied to the NEMS resonator;
(d) multiplexing the frequency varying signals together into a single readout signal path;
(e) continuously monitoring the multiplexed frequency varying signals in the common readout path to determine variations in vibrational amplitude of the frequency varying signals; and
(f) deconvolving the multiplexed frequency varying signals in the common readout path to recover and uniquely identify the output electrical potential.

9. The method of claim 8, wherein:
each piezoelectric NEMS resonator comprises a resonant member including a semiconductor p-type/intrinsic/n-type (PIN) diode;
a charge depleted high resistance region or depletion region in a middle of the PIN diode forms a piezoelectrically active layer;
each piezoelectric NEMS resonator is tuned to a unique frequency by designing each resonant member to have a different length;
an AC signal is applied across the PIN diode to produce a strain on the piezoelectrically active layer;
the AC signal comprises the one or more output electrical potentials from the voltage sensitive device; and
said strain results in an actuation or mechanical resonance of the resonant member at or near its resonance frequency.

10. The method of claim 8, wherein:
each piezoelectric NEMS resonator comprises:
a movable member including a region of low conductivity over which an electric field is developed wherein a region width is within a factor of ten (10) of a thickness of the NEMS resonator;
wherein the region is formed between a junction that incorporates piezoelectric material, wherein applying a first voltage across the region alters a width of an active portion of the region thereby adjusting a movement of the movable member induced by the output electrical potentials;
wherein the output electrical potentials are applied across the region to produce a strain on the active portion of the region, wherein said strain results in a defined movement of the movable member.

11. The method of claim 8, wherein:
the voltage sensitive device is configured to detect and output a microvolt; and
the array of piezoelectric NEMS resonators convert the microvolt size electrical potential to the corresponding frequency varying signal.

12. The method of claim 8, wherein the array of NEMS resonators are used to produce a nanomechanical Fourier transform.

13. The method of claim 8, wherein the unique frequency that each NEMS resonator is tuned to is in the range of several megahertz to over one gigahertz thereby increasing a number of the frequency varying signals that are multiplexed into the common readout path.

14. The method of claim 8, wherein:
the voltage sensitive device comprises an implantable neural probe comprising a grid of recording site electrodes; and
each recording site electrode is communicatively coupled to one of the piezoelectric NEMS resonators.

* * * * *